US012699110B2

(12) United States Patent (10) Patent No.: US 12,699,110 B2
Okada et al. (45) Date of Patent: *Aug. 4, 2026

(54) CELL PICKING DEVICE

(71) Applicant: SHIMADZU CORPORATION, Kyoto (JP)

(72) Inventors: Mika Okada, Kyoto (JP); Akari Takeda, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 874 days.

This patent is subject to a terminal disclaimer.

(21) Appl. No.: 17/626,841

(22) PCT Filed: Jul. 26, 2019

(86) PCT No.: PCT/JP2019/029513
§ 371 (c)(1),
(2) Date: Jan. 13, 2022

(87) PCT Pub. No.: WO2021/019623
PCT Pub. Date: Feb. 4, 2021

(65) Prior Publication Data
US 2022/0276271 A1 Sep. 1, 2022

(51) Int. Cl.
*G01N 35/00* (2006.01)
*B01L 3/02* (2006.01)
(Continued)

(52) U.S. Cl.
CPC .......... *G01N 35/0099* (2013.01); *B01L 3/021* (2013.01); *B01L 9/54* (2013.01);
(Continued)

(58) Field of Classification Search
CPC ......... G01N 35/0099; G01N 2035/103; G01N 2035/1053; G01N 35/1011; B01L 3/021;
(Continued)

(56) References Cited

U.S. PATENT DOCUMENTS 4,707,337 A * 11/1987 Jeffs ...................... B01L 3/0275
422/931
7,964,160 B2 6/2011 Zuppiger et al.
(Continued)

FOREIGN PATENT DOCUMENTS

CN 204602216 U 9/2015
CN 109387512 A 2/2019
(Continued)

OTHER PUBLICATIONS

Decision of Refusal for corresponding Chinese Patent Application No. 201980098273.5 dated Jul. 4, 2024, with English machine translation.
(Continued)

*Primary Examiner* — Maris R Kessel
*Assistant Examiner* — Valerie Simmons
(74) *Attorney, Agent, or Firm* — Renner, Otto, Boisselle & Sklar, LLP

(57) ABSTRACT

A suction arm advances in an axial direction of a pipette tip such that an end of the pipette tip comes into contact with a bottom surface of a sample container while the pipette tip attached to a suction arm is tilted with respect to a vertical direction. Next, the suction arm is moved such that the end of the pipette tip scans the bottom surface of the sample container in a horizontal direction toward a predetermined position. Subsequently, at the predetermined position, the suction arm is further tilted by a predetermined angle such that the end of the pipette tip is lifted and a base of the pipette tip is lowered. Thereafter, the suction arm performs a sucking operation such that a sample is sucked through the end of the pipette tip.

11 Claims, 13 Drawing Sheets

(51) Int. Cl.
| | | |
|---|---|---|
| *B01L 9/00* | (2006.01) | |
| *B25J 15/06* | (2006.01) | |
| *C12M 1/32* | (2006.01) | |
| *G01N 35/10* | (2006.01) | |

(52) U.S. Cl.
CPC .......... *B25J 15/0616* (2013.01); *C12M 23/12* (2013.01); *G01N 2035/103* (2013.01); *G01N 2035/1053* (2013.01)

(58) Field of Classification Search
CPC ....... B01L 9/54; B25J 15/0616; C12M 23/12; C12M 33/04; C12M 41/48; C12Q 1/02; C12Q 1/24
See application file for complete search history.

(56) References Cited

U.S. PATENT DOCUMENTS

| | | | |
|---|---|---|---|
| 10,357,767 | B1 | 7/2019 | Sternick |
| 12,099,072 | B2 | 9/2024 | Okada et al. |
| 2004/0067170 | A1 | 4/2004 | Higuchi |
| 2005/0106718 | A1 | 5/2005 | Balasubramanian et al. |
| 2006/0051735 | A1 | 3/2006 | Fuhr et al. |
| 2007/0038411 | A1 | 2/2007 | Taki et al. |
| 2008/0089811 | A1* | 4/2008 | Hecht ................... B01L 3/0275 |
| | | | 422/400 |
| 2008/0264187 | A1* | 10/2008 | Angus ................... B01L 3/0279 |
| | | | 73/864.14 |
| 2013/0027539 | A1 | 1/2013 | Kiyota et al. |
| 2016/0139166 | A1 | 5/2016 | Berberich et al. |
| 2016/0169775 | A1 | 6/2016 | Kei |
| 2016/0334429 | A1* | 11/2016 | Abe ................... G01N 35/0099 |
| 2017/0061078 | A1 | 3/2017 | Natsume et al. |
| 2017/0203290 | A1 | 7/2017 | Ando et al. |
| 2018/0079999 | A1 | 3/2018 | Blanchard |
| 2018/0087020 | A1 | 3/2018 | Blanchard |
| 2018/0087021 | A1 | 3/2018 | Blanchard |
| 2018/0119086 | A1 | 5/2018 | Markussen et al. |
| 2018/0346868 | A1 | 12/2018 | Blanchard |
| 2019/0031993 | A1 | 1/2019 | Matsunaga |
| 2019/0039070 | A1 | 2/2019 | Matsunaga |
| 2019/0049357 | A1 | 2/2019 | Matsumoto et al. |
| 2019/0145995 | A1* | 5/2019 | Black ....................... G01N 1/38 |
| | | | 422/511 |
| 2019/0381495 | A1* | 12/2019 | Tanaka ................... B01L 3/0286 |
| 2020/0065363 | A1 | 2/2020 | Yamane et al. |
| 2020/0248132 | A1 | 8/2020 | Markussen et al. |
| 2020/0347339 | A1 | 11/2020 | Blanchard |
| 2020/0377833 | A1* | 12/2020 | Inoue ..................... C12M 1/265 |
| 2021/0179990 | A1 | 6/2021 | Zhu |
| 2021/0222110 | A1 | 7/2021 | Blanchard |
| 2021/0261903 | A1 | 8/2021 | Blanchard |
| 2022/0089997 | A1 | 3/2022 | Blanchard |
| 2022/0178961 | A1* | 6/2022 | Ezure ..................... C12M 47/02 |
| 2022/0243167 | A1 | 8/2022 | Blanchard |
| 2022/0259546 | A1 | 8/2022 | Blanchard |
| 2022/0276271 | A1 | 9/2022 | Okada et al. |

FOREIGN PATENT DOCUMENTS

| | | | |
|---|---|---|---|
| CN | 111712561 | A | 9/2020 |
| JP | 2012208234 | A | 10/2012 |
| JP | 2016-112012 | A | 6/2016 |
| JP | 2018-510659 | A | 4/2018 |
| JP | 2020120618 | A | 8/2020 |
| WO | 2016/147239 | A1 | 9/2016 |
| WO | 2016/150446 | A1 | 9/2016 |
| WO | 2017/170993 | A1 | 10/2017 |
| WO | 2019/018152 | A1 | 1/2019 |
| WO | 2019/176093 | A1 | 9/2019 |

OTHER PUBLICATIONS

Office Action in corresponding Chinese Patent Application No. 201980098273.5 dated Dec. 11, 2023, with English machine translation.
Decision of Refusal for corresponding Chinese Patent Application No. 201980098792.1 dated Jun. 5, 2024, with English machine translation.
Office Action for corresponding Chinese Patent Application No. 201980098273.5 dated Jun. 3, 2024, with English machine translation.
Final Office Action issued in the related U.S. Appl. No. 17/533,850.
Frohlich et al.; "New techniques for isolation of single prokaryotic cells"; FEMS Microbiology Reviews. 24 (2000) 567-572.
Office Action issued in co-pending U.S. Appl. No. 17/533,850 dated Sep. 9, 2024.
Office Action for U.S. Appl. No. 17/533,850 dated Nov. 2, 2023.
Office Action for U.S. Appl. No. 17/628,029 dated Jun. 9, 2023.
Office Action for U.S. Appl. No. 17/628,029 dated Oct. 27, 2023.
Office Action Advisory Action for U.S. Appl. No. 17/628,029 dated Mar. 6, 2024.
Berg et al., "Evaluation of liquid handling conditions in microplates". J Biomol Screen. 2001; 6(1): p. 47-56. doi:10.1177/108705710100600107 (Year: 2001).
Office Action for U.S. Appl. No. 16/969,859 dated Aug. 8, 2023.
International Search Report for corresponding Application No. PCT/JP2019/029513, mailed Oct. 21, 2019.
Written Opinion for corresponding Application No. PCT/JP2019/029513, mailed Oct. 21, 2019 (English machine translation).
International Search Report for PCT/JP2019/029512, dated Oct. 15, 2019.
Written Opinion for PCT/JP2019/029512, dated Oct. 15, 2019, with partial English translation.
Notification of Reasons for Refusal dated Dec. 20, 2022 from the Japanese Patent Office in Application No. 2021-536466, with English machine translation.
Office Action for Chinese Patent Application No. 201980098792.1 dated Dec. 11, 2023, with English machine translation.
International Search Report with respect to International Patent Application No. PCT/JP2018/010488, mailed Jun. 19, 2018.
Written Opinion of the International Searching Authority with respect to International Patent Application No. PCT/JP2018/010488 (English Machine Translation), mailed Jun. 19, 2018.
Office Action for Chinese Patent Application No. 201880089296.5 dated Dec. 21, 2022, with English machine translation.
Practical Handbook of Middle School Chemistry Experiments, Education Science Press, p. 28, May 31, 1991, with partial English translation.
Notice of Decision of Refusal in Chinese Patent Application No. 201880089296.5 dated Mar. 31, 2023, with English machine translation.
Office Action for corresponding Chinese Patent Application No. 202111477180.9 dated Aug. 29, 2024, with English machine translation.
Decision of Refusal in corresponding Chinese Patent Application No. 202111477180.9 dated Nov. 29, 2024, with English machine translation.
Review Notice of Determination in the corresponding Chinese Patent Application No. 202111477180.9 dated Aug. 14, 2025, with English machine translation.
Review Notification in the related Chinese patent Application No. 202111477180.9 dated Jun. 3, 2025, with English machine translation.

* cited by examiner

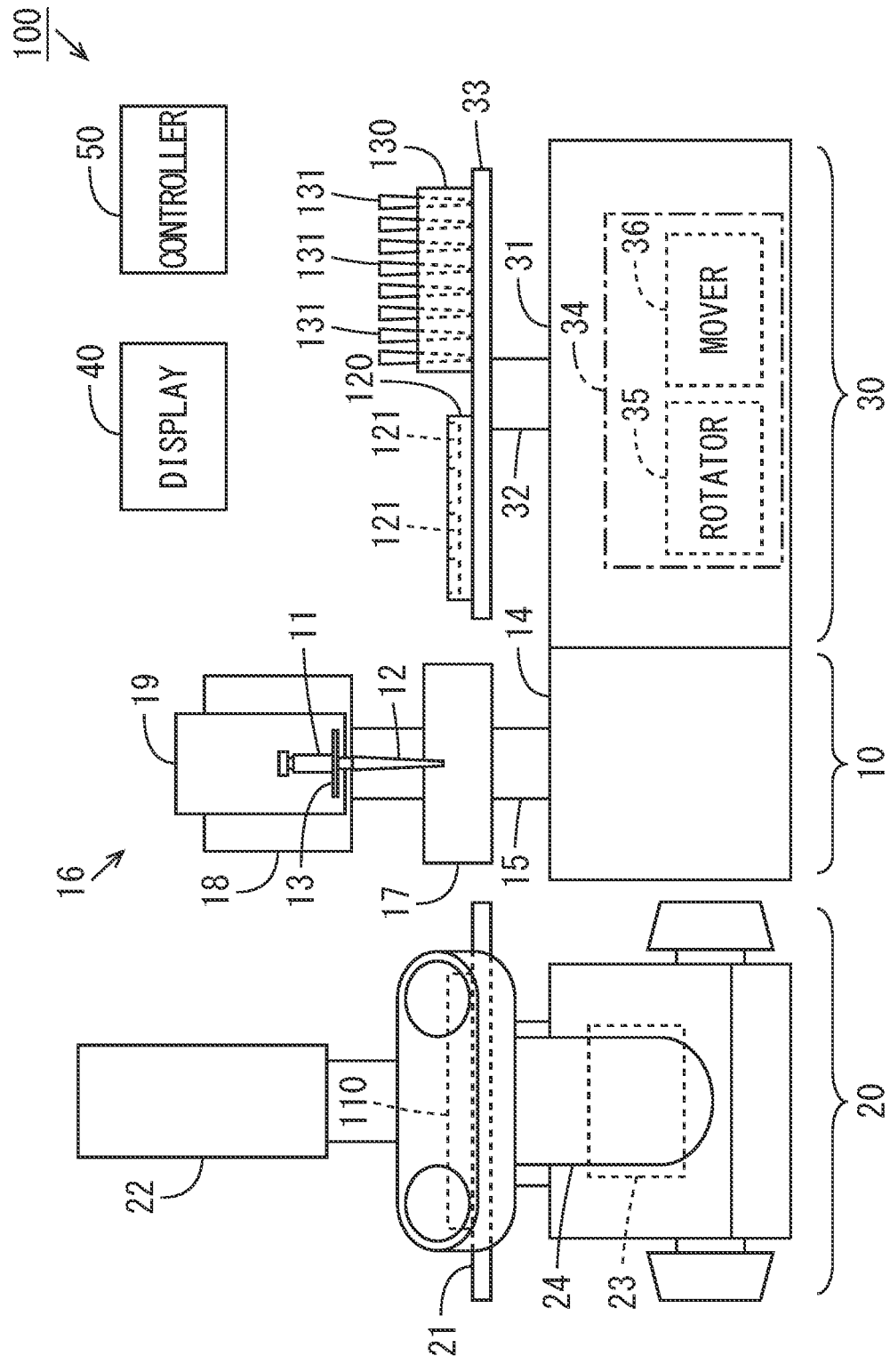
F I G .   1

F I G .  2
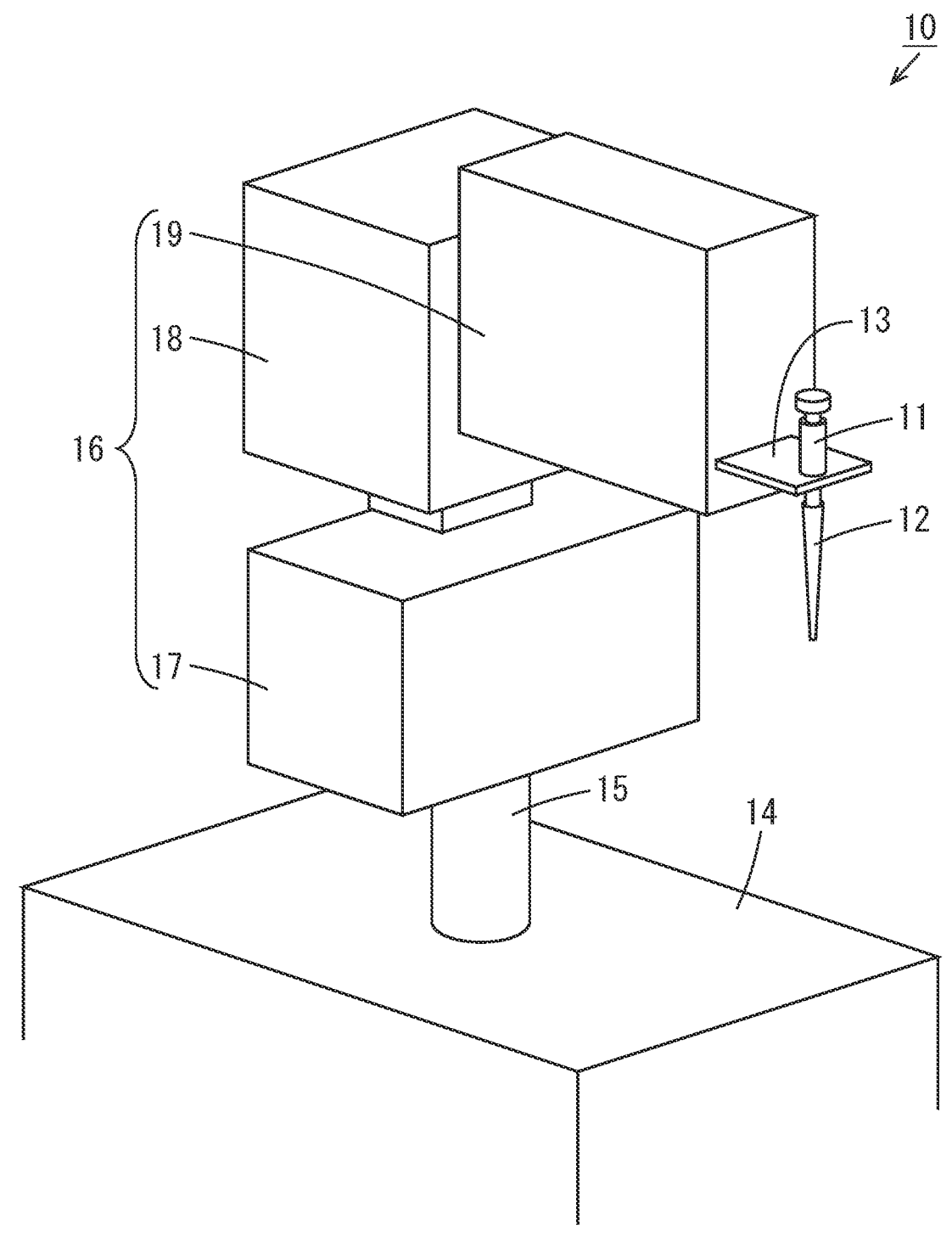

F I G. 4
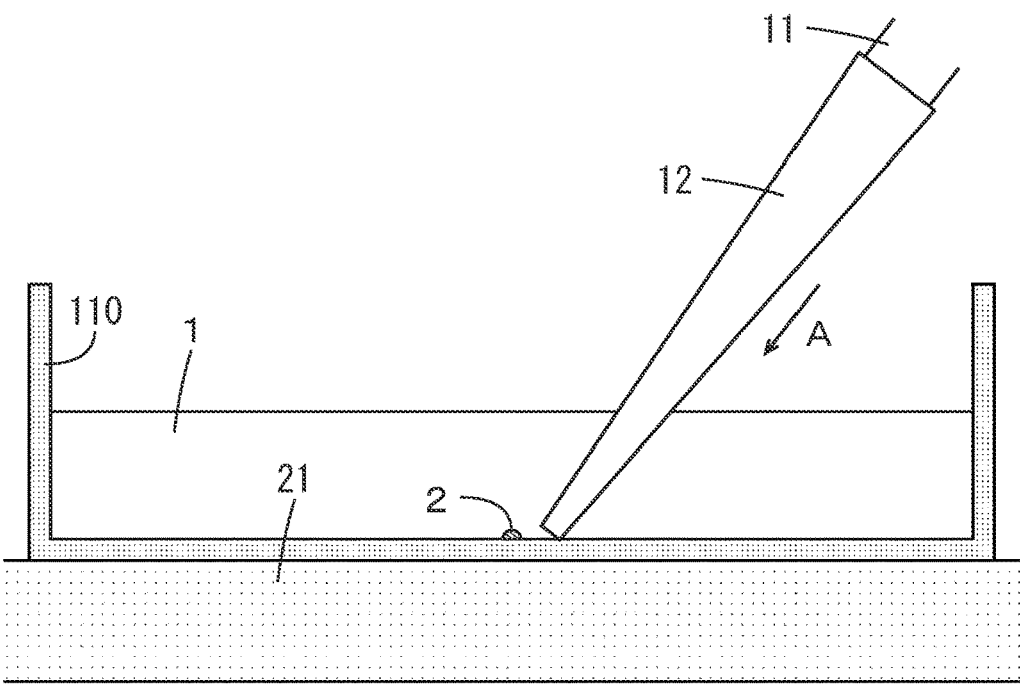
F I G. 5
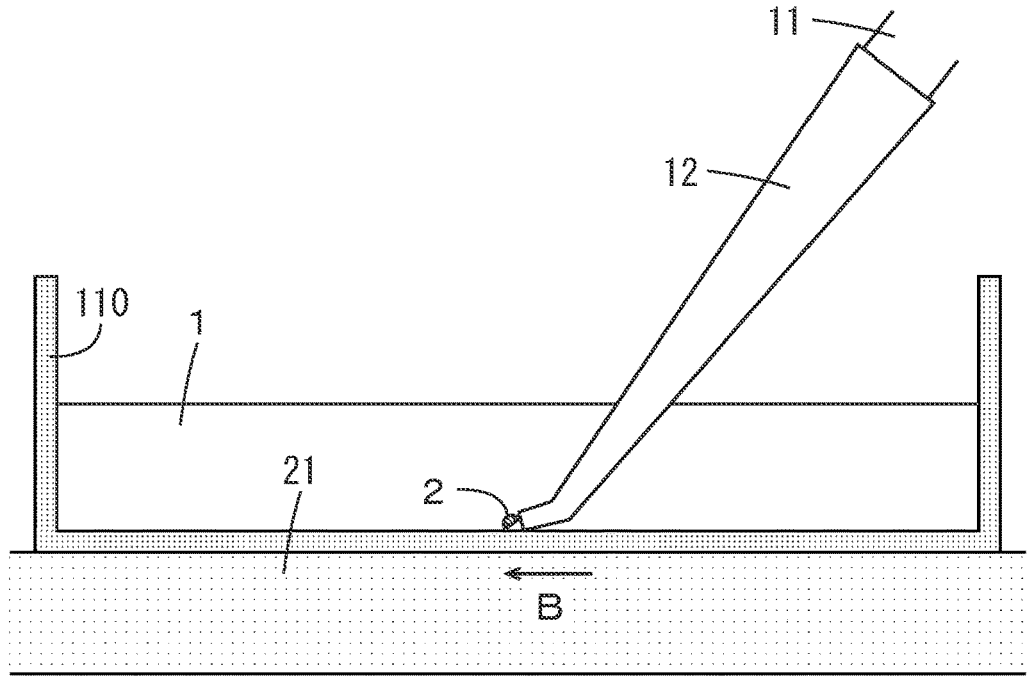

F I G .  6
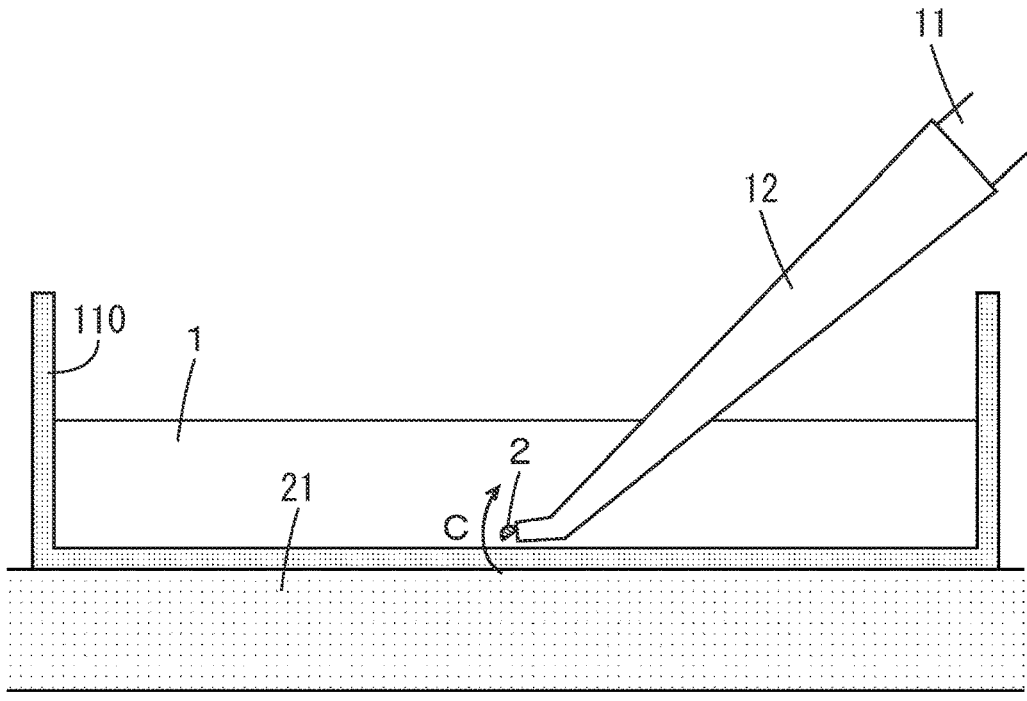
F I G .  7
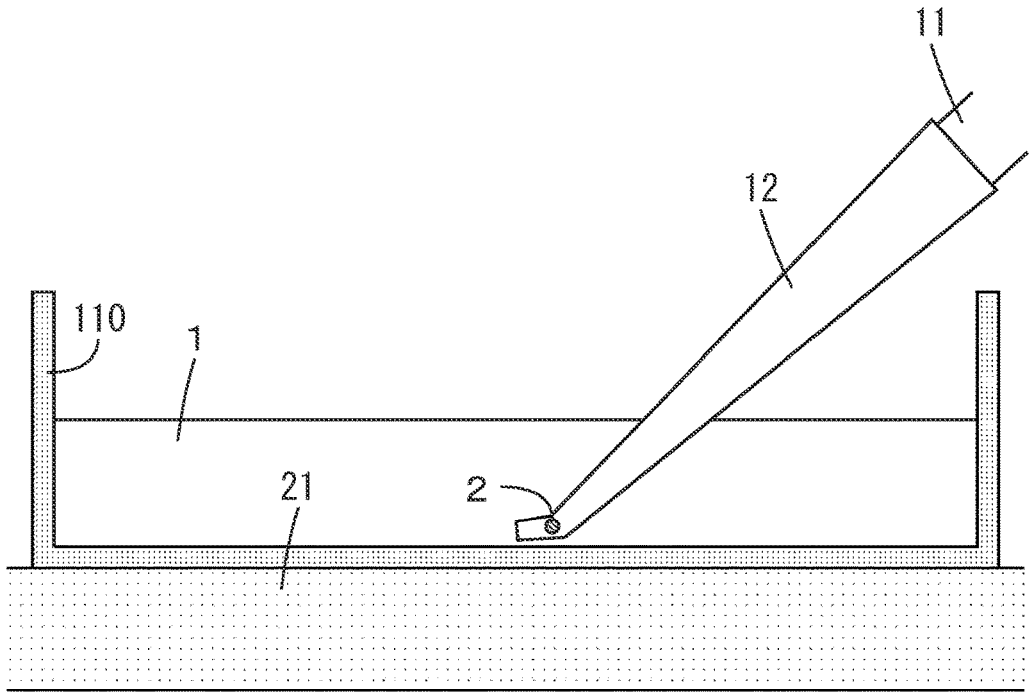

F I G. 8
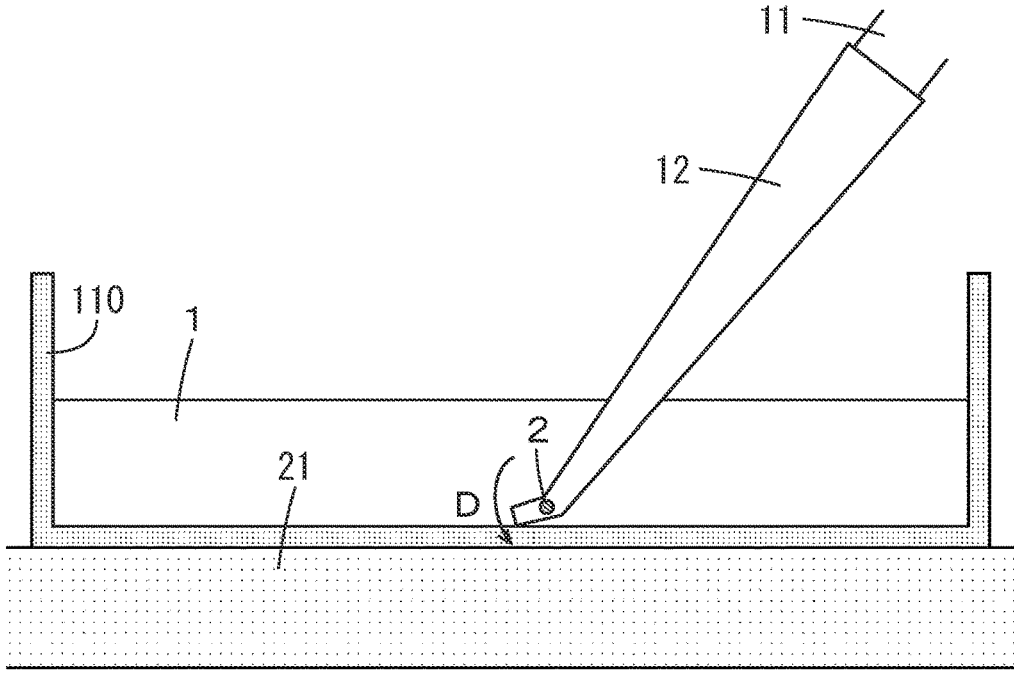
F I G. 9
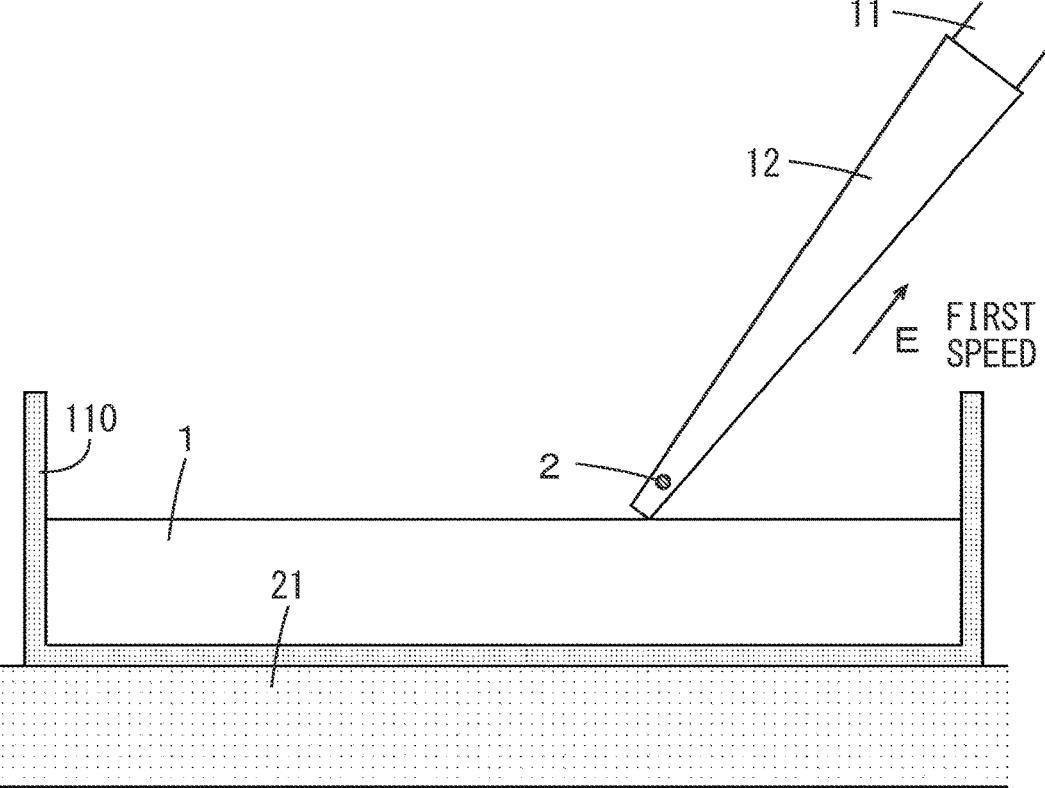

F I G. 1 0
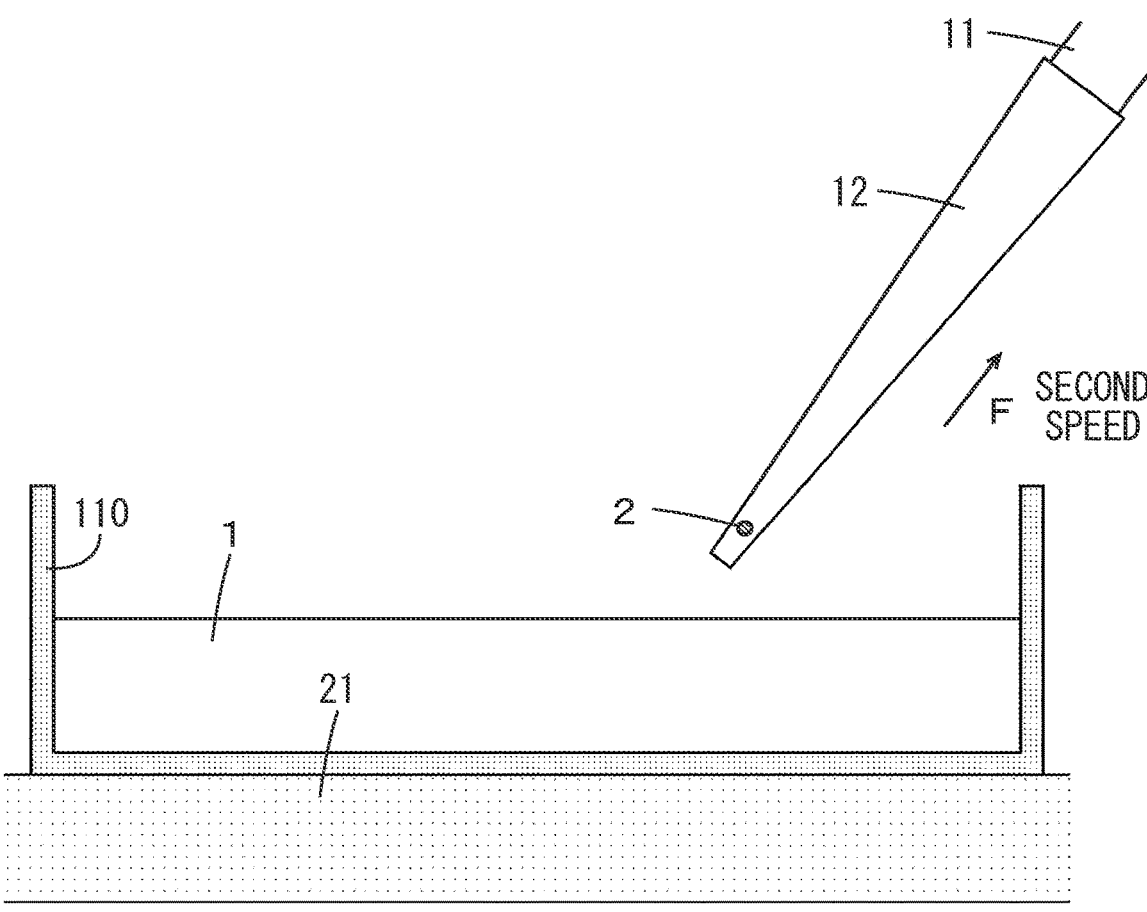

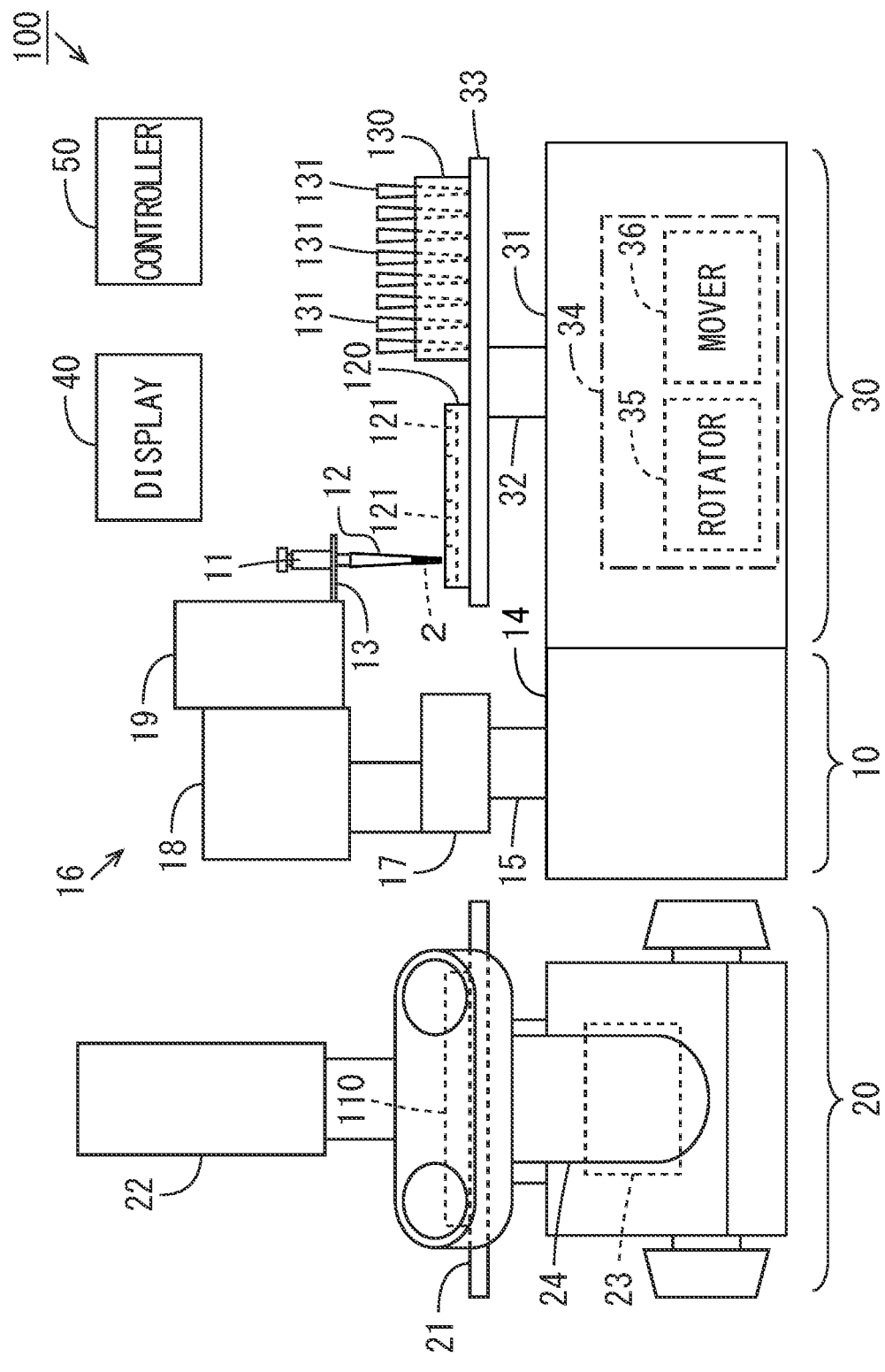
F I G.  1 1

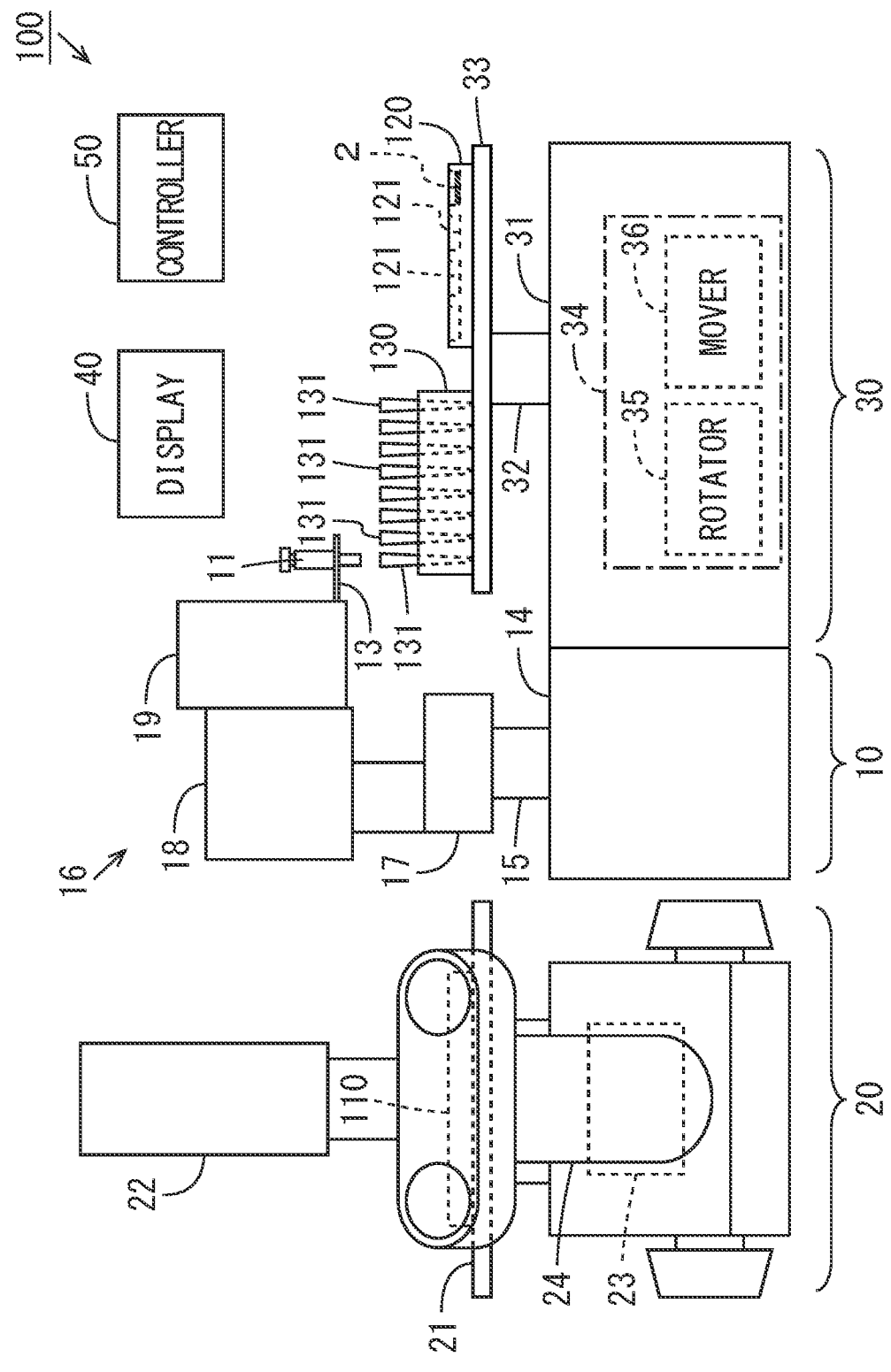
F I G .  1 2

F I G.  1 4
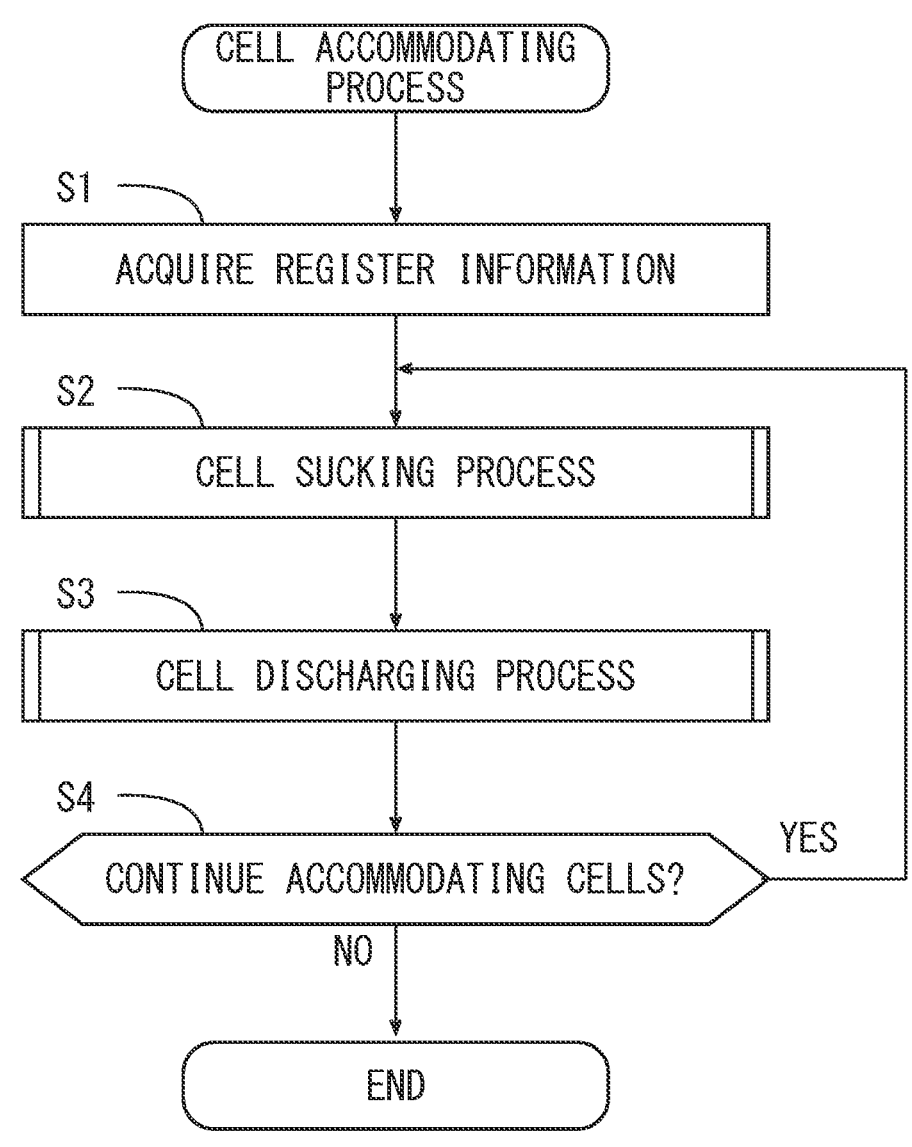

F I G .  1 5
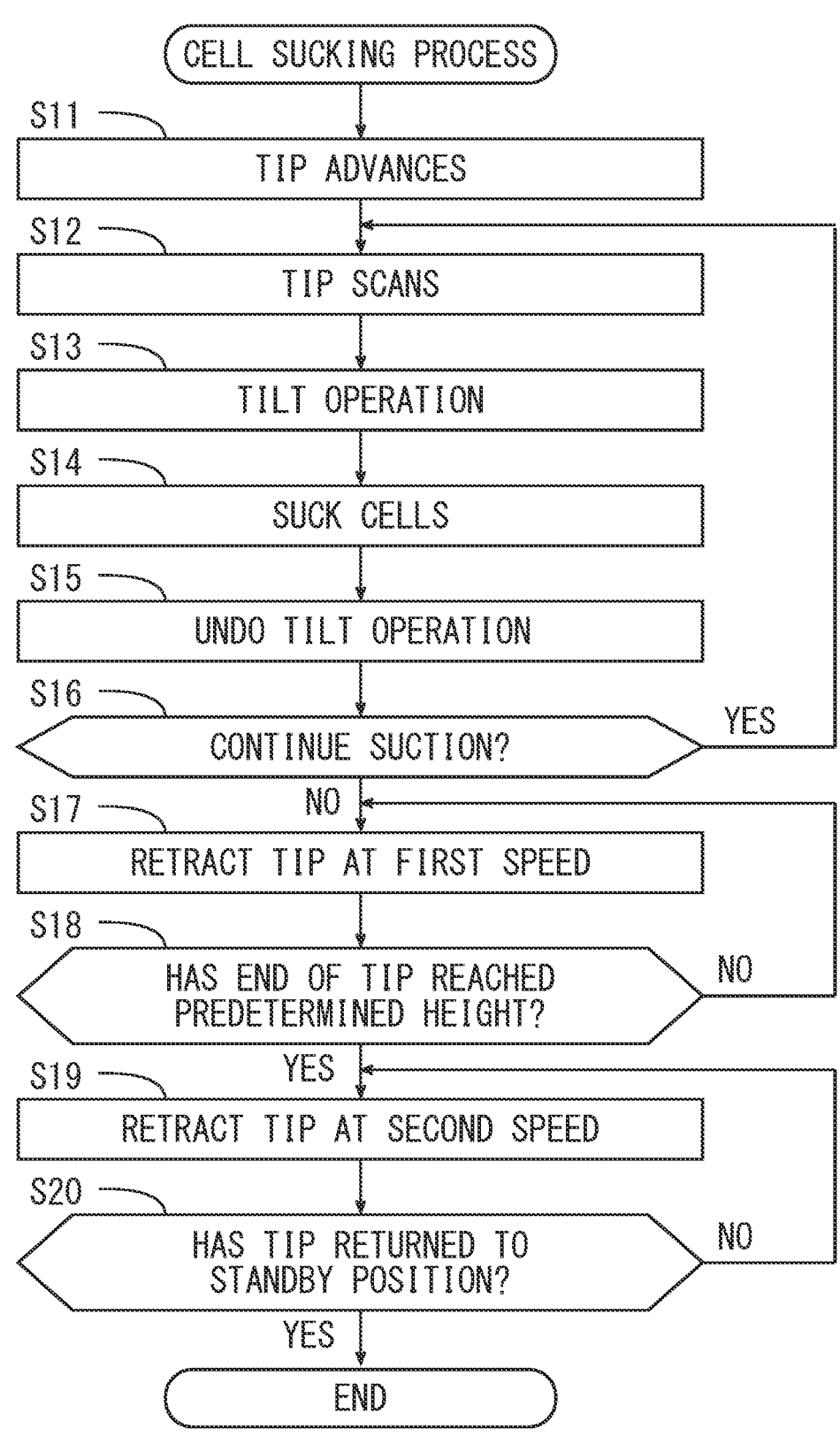

F I G.  1 6
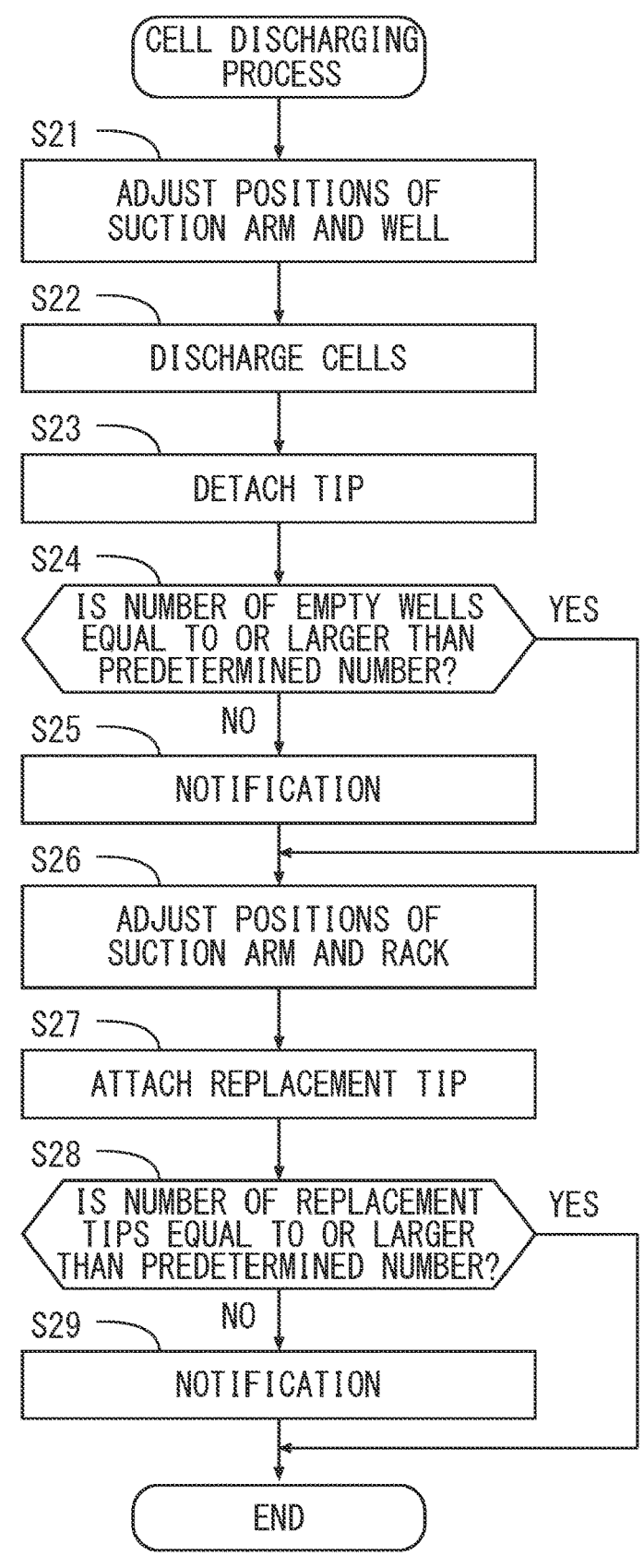

CELL PICKING DEVICE

TECHNICAL FIELD

The present invention relates to a cell picking device.

BACKGROUND ART

In a case where specific cells are to be sucked from a container such as a cell culture container, a worker sucks the cells manually using a suction tool such as a pipette while checking the position of the subject cells with a microscope. However, since such work requires skill, an unskilled worker cannot easily suck cells. As such, a cell-sucking system that assists cell-sucking work has been suggested (see Patent Document 1, for example.)

In the cell-sucking system described in Patent Document 1, a tubular tip for sucking cells contained in a container is attached to a sucker. The position of the sucker is adjusted three-dimensionally by a transporter such that the end of the tip is in close proximity to specific cells.

[Patent Document 1] JP 2016-112012 A

SUMMARY OF INVENTION

Technical Problem

In the above-mentioned cell-sucking system, the smaller the subject cells are, the higher the moving resolution of the sucker is required to be. Therefore, in a case where cells and the end of the tip are largely separated from each other, it requires a long period of time to guide the end of a tip into the cells, and efficiency of sucking work is degraded. Further, because being adsorbed to a bottom surface of the container, the cells are not necessarily sucked efficiently into the tip.

An object of the present invention is to provide a cell picking device that can efficiently suck cells in a sample.

Solution to Problem

One aspect according to the present invention relates to a cell picking device for sucking cells from a liquid sample in a sample container that includes a suction arm to which a pipette tip is attachable, a first driver that drives the suction arm and causes the suction arm to perform a sucking operation, and a controller that controls an operation of the first driver, wherein the controller includes an advancer that advances the suction arm in an axial direction of the pipette tip such that an end of the pipette tip comes into contact with a bottom surface of the sample container while tilting the pipette tip attached to the suction arm with respect to a vertical direction, a scanner that moves the suction arm such that an end of the pipette tip scans a bottom surface of the sample container in a horizontal direction toward a predetermined position, a tilter that further tilts the suction arm by a predetermined angle such that an end of the pipette tip is lifted and a base of the pipette tip is lowered at the predetermined position, and a sucker that causes the suction arm to perform a sucking operation such that a sample is sucked through an end of the pipette tip.

Advantageous Effects of Invention

With the present invention, cells in a sample can be sucked efficiently.

BRIEF DESCRIPTION OF THE DRAWINGS

FIG. 1 is a schematic diagram showing the configuration of a cell picking device according to one embodiment of the present invention.

FIG. 2 is a schematic diagram showing the configuration of a suction device of FIG. 1.

FIG. 4 is a diagram for explaining the cell sucking operation performed by the suction device.

FIG. 5 is a diagram for explaining the cell sucking operation performed by the suction device.

FIG. 6 is a diagram for explaining the cell sucking operation performed by the suction device.

FIG. 7 is a diagram for explaining the cell sucking operation performed by the suction device.

FIG. 8 is a diagram for explaining the cell sucking operation performed by the suction device.

FIG. 9 is a diagram for explaining the cell sucking operation performed by the suction device.

FIG. 10 is a diagram for explaining the cell sucking operation performed by the suction device.

FIG. 11 is a diagram for explaining the cell discharging operation performed by the suction device.

FIG. 12 is a diagram for explaining the cell discharging operation performed by the suction device.

FIG. 14 is a flowchart showing one example of the algorithm of a cell accommodating process executed by a controller.

FIG. 15 is a flowchart showing one example of the algorithm of a cell sucking process of FIG. 14 executed by a suction processor.

FIG. 16 is a flowchart showing one example of the algorithm of a cell discharging process of FIG. 14 executed by a discharge processor.

DESCRIPTION OF EMBODIMENTS

(1) Configuration of Cell Picking Device

Figure 3:
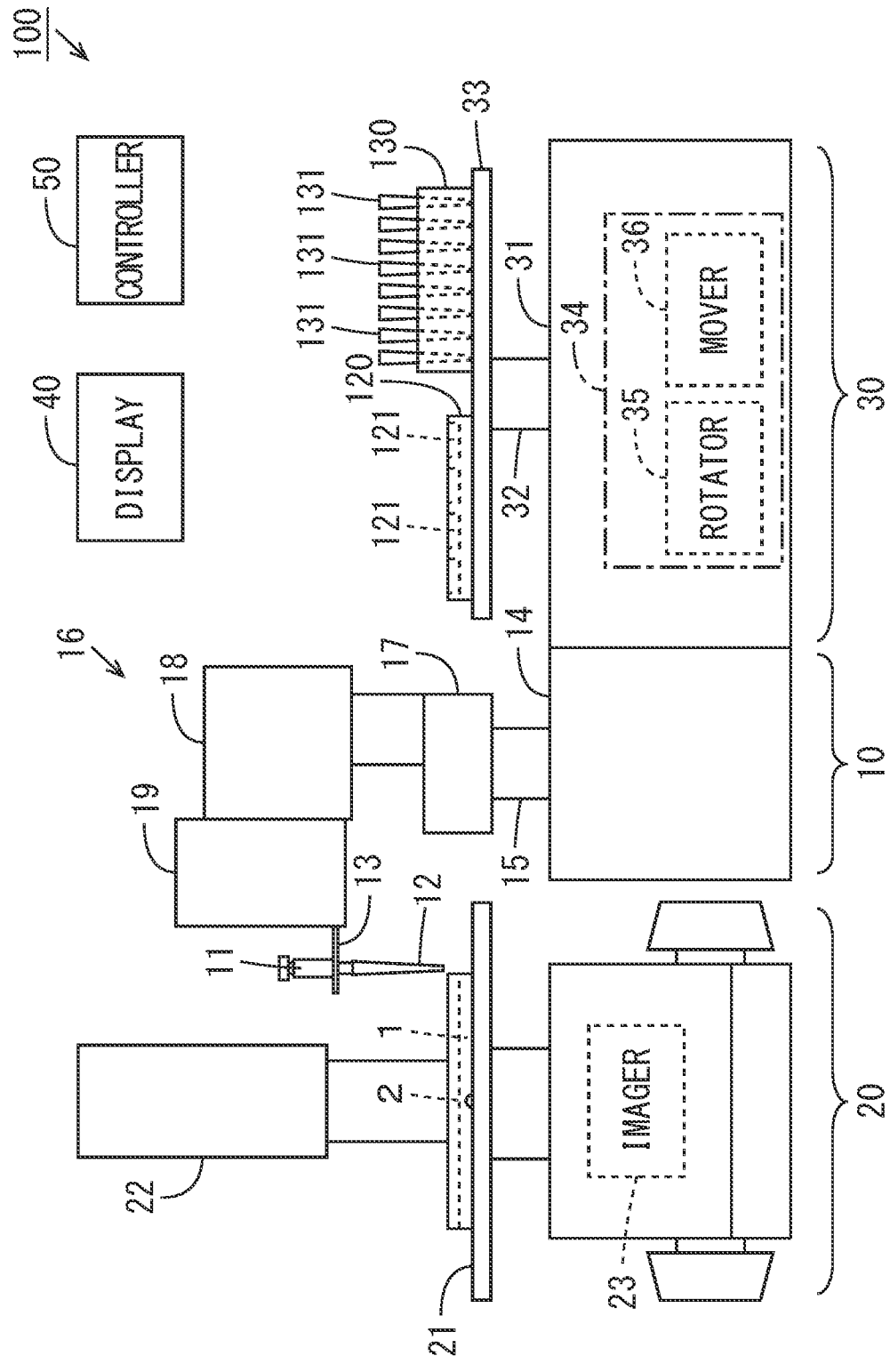
FIG. 3 is a diagram for explaining a cell sucking operation performed by the suction device.

A cell picking device according to embodiments of the present invention will be described below in detail with reference to the drawings. FIG. 1 is a schematic diagram showing the configuration of the cell picking device according to one embodiment of the present invention. As shown in FIG. 1, the cell picking device 100 includes a suction device 10, an observation device 20, a plate changer 30, a display 40 and a controller 50. Further, the cell picking device 100 is provided with a sample container 110, a culture plate 120 and a pipette tip rack 130 (hereinafter simply referred to as a rack 130).

The sample container 110 is a petri plate, for example, and accommodates a sample including cells. The culture plate 120 is a multi-well plate in which a plurality of wells are arranged and used for culturing of cells. The rack 130 holds a plurality of replacement pipette tips 131 (hereinafter simply referred to as replacement tips 131). In the present example, 24 wells 121 are arranged in 4 rows by 6 columns in the culture plate 120. Further, 96 replacement tips 131 are held while being arranged in 8 rows by 12 columns in the rack 130.

The suction device 10 includes a pipette-shape suction arm 11. Any replacement tip 131 held in the rack 130 is attached to the end of the suction arm 11. Hereinafter, a replacement tip 131 attached to the suction arm 11 is simply referred to as a tip 12. The suction device 10 sucks cells in the sample container 110 through the tip 12 and discharges (seeds) the cells to any well 121 of the culture plate 120. Thereafter, a similar operation is repeated using a new replacement tip 131 and a new well 121. Details of the configuration and operation of the suction device 10 will be described below.

The observation device 20 includes a stage 21, an illuminator 22, an imager 23 and a microscope 24 and is arranged to be adjacent to the suction device 10. The sample container 110 is placed on the stage 21. The illuminator 22 is arranged above the stage 21. The illuminator 22 includes a light source such as a light emitting diode, for example, and illuminates the sample container 110 placed on the stage 21. The stage 21 is translucent. Alternatively, an opening through which light from the illuminator 22 passes downwardly may be formed in the stage 21.

The imager 23 is arranged below the stage 21. The imager 23 includes a plurality of lenses, a camera and so on, and picks up an image while magnifying a sample in the sample container 110 illuminated by the illuminator 22. The microscope 24 includes an eyepiece, a lens-barrel, an objective lens, etc., and is used by a user when a sample in the sample container 110 placed on the stage 21 is magnified for observation.

The plate changer 30 is an optional device arranged to be opposite to the observation device 20 with the suction device 10 provided therebetween and is configured to be attachable to and detachable from the suction device 10. The plate changer 30 includes a base 31, a vertical shaft 32, a platform 33 and a driver 34. The vertical shaft 32 is provided to extend in an up-and-down direction in the base 31. An upper portion of the vertical shaft 32 projects from the base 31. The platform 33 is attached to the upper end of the vertical shaft 32 in a horizontal attitude. The culture plate 120 and the rack 130 are placed on the platform 33.

The driver 34 includes a rotator 35 and a mover 36, and is connected to the platform 33 through the vertical shaft 32 in the base 31. The rotator 35 includes an electric motor, for example, and rotates the platform 33 in a horizontal plane. Thus, the culture plate 120 and the rack 130 placed on platform 33 are selectively moved to the vicinity of the suction device 10.

Specifically, when the suction device 10 discharges cells into any well 121, the culture plate 120 is moved to the vicinity of the suction device 10. On the other hand, when any replacement tip 131 is attached to the suction arm 11, the rack 130 is moved to the vicinity of the suction device 10. With this configuration, an increase in moving range of the platform 33 is prevented.

The mover 36 includes a stepping motor, for example, and moves the platform 33 in parallel with a horizontal plane. Specifically, the mover 36 moves any well 121 of the culture plate 120 or any replacement tip 131 in the rack 130 to a position accessible by the suction arm 11 (below the suction arm 11, for example). Thus, cells can be discharged from the suction device 10 into a well 121, or a replacement tip 131 can be attached to the suction arm 11.

The display 40 includes an LCD (Liquid Crystal Display) panel or an organic EL (Electroluminescence) panel, for example, and displays an image or the like generated by the imager 23 of the observation device 20. The controller 50 includes a personal computer, for example, and includes a CPU (Central Processing Unit), a memory and so on. Further, the controller 50 controls the operations of the suction device 10 and the plate changer 30.

(2) Configuration of Suction Device

FIG. 2 is a schematic diagram showing the configuration of the suction device 10 of FIG. 1. As shown in FIG. 2, the suction device 10 includes a suction arm 11, a tip 12, a holder 13, a base 14, a vertical shaft 15 and a driver 16. The driver 16 includes rotators 17, 18 and a suction driver 19. The holder 13 holds the suction arm 11 at the suction driver 19. The vertical shaft 15 is provided on the upper surface of the base 14 to extend in the up-and-down direction.

The rotator 17 includes an electric motor, for example, and is attached to the upper end of the vertical shaft 15 to be rotatable in a horizontal plane. The rotator 18 includes an electric motor, for example, and is attached to the rotator 17 to be rotatable in a vertical plane. The rotator 17 and the rotator 18 may be constituted by a single electric motor, etc. which is rotatable in the horizontal plane and the vertical plane.

The suction driver 19 includes a stepping motor, for example, and is attached to the rotator 18 to be advanceable and retreatable in a predetermined direction (an up-and-down direction in a case where the rotator 18 is not rotating in the vertical plane). Further, the suction driver 19 includes a suction mechanism and is configured to be capable of sucking and discharging cells using the suction arm 11. Further, the suction driver 19 includes a tip detachment mechanism and is configured to be capable of detaching the tip 12 from the end of the suction arm 11.

(3) Cell Sucking Operation

FIGS. 3 to 10 are diagrams for explaining a cell sucking operation performed by the suction device 10. As shown in FIG. 3, a predetermined volume of a liquid sample 1 is accommodated in the sample container 110 placed on the stage 21. Cells 2 to be sucked are included in the sample 1. The cells 2 are adsorbed to a bottom surface of the sample container 110 at a substantially center portion of the sample container 110. In FIG. 3, the microscope 24 is not shown in order to facilitate viewing of the stage 21 and the sample container 110.

During the cell sucking operation, the rotator 17 is rotated in a horizontal plane such that the suction arm 11 and the tip 12 are directed toward the observation device 20. Further, the rotator 18 is rotated in a vertical plane such that the tip 12 attached to the suction arm 11 is tilted by a predetermined angle. The position of the tip 12 at this time is referred to as a standby position.

Next, the suction driver 19 moves toward the end of the tip 12 in the axial direction of the tip 12. In this case, as indicated by the arrow A in FIG. 4, the end of the tip 12 comes into contact with the bottom surface of the sample container 110. Here, the end of the tip 12 may be bent slightly elastically by the pressure of the end of the tip 12 against the bottom surface of the sample container 110 (see FIG. 5.)

Subsequently, the suction driver 19 further moves toward the end of the tip 12. In this case, as indicated by the arrow B in FIG. 5, the tip 12 scans the bottom surface of the sample container 110 toward the center portion of the sample container 110. As a result, the end of the tip 12 comes into contact with the cells 2, and the cells 2 adsorbed to the bottom surface of the sample container 110 are separated.

Thereafter, the rotator 18 is slightly rotated in a vertical plane such that the tip 12 is further tilted. Thus, as indicated by the arrow C in FIG. 6, the end of the tip 12 is lifted slightly, the base of the tip 12 is lowered slightly and the cells 2 are stripped from the bottom surface of the sample container 110. In the following description, the above-mentioned operation of tilting the tip 12 is referred to as a tilt operation.

A tilt angle of the tip 12 during the tilt operation is preferably larger than 0 degree, for example. In this case, the cells 2 can be easily stripped from the bottom surface of the sample container 110. Further, the tilt angle of the tip 12 during the tilt operation is preferably equal to or smaller than 2 degrees, for example. In this case, the end of the tip 12 is prevented from moving out of the visual field of the microscope 24 of FIG. 1. Thus, the user can easily magnify and observe the end of the tip 12.

Next, as shown in FIG. 7, the cells 2 are sucked into the tip 12 by an operation of the suction mechanism of the suction driver 19. In the present example, the above-mentioned suction is started at a point in time that is later than the start of the tilt operation and earlier than the stop of the tilt operation, and suction is stopped after a predetermined period of time elapses from a point in time at which the tilt operation is stopped. In this case, the cells 2 are sucked efficiently.

However, the timing for suction is not limited to the above-mentioned example. Suction may be started at a point in time later than the stop of the tilt operation or suction may be started at the same time as the start of the tilt operation. Alternatively, suction may end at a point in time earlier than the end of the tilt operation, or suction may be stopped at the same time as the stop of the tilt operation.

After the end of suction of the cells 2, the rotator 18 is slightly rotated backward in a vertical plane. Thus, as indicated by the arrow Din FIG. 8, the end of the tip 12 is slightly lowered, the base of the tip 12 is slightly lifted and the attitude of the tip 12 returns to the attitude prior to the tilt operation. That is, the tilt operation is undone. In this case, the operation of FIGS. 4 to 8 is repeated, so that successive suction of the cells 2 can be carried out easily. In the successive suction of the cells 2, the rotator 17 may be slightly rotated in a horizontal plane after the operation of FIG. 8. In this case, the cells 2 located at a position slightly different from the previous suction position can be sucked.

After the suction of the cells 2, the suction driver 19 moves toward the rear end of the tip 12 in the axial direction of the tip 12 by a predetermined distance at a predetermined first speed. In this case, as indicated by the arrow E in FIG. 9, the tip 12 is lifted at the first speed. The tip 12 continues to be lifted at the first speed until the end of the tip 12 reaches a predetermined height. In the present example, the predetermined height is the height of a liquid surface of the sample 1. The height of the liquid surface of the sample 1 may be estimated based on the depth of the sample container 110. Further, the position of the end of the tip 12 may be determined based on the number of pulses of the stepping motor of the suction driver 19.

Thereafter, the suction driver 19 further moves toward the end of the tip 12 in the axial direction of the tip 12 by a predetermined distance at a second speed larger than the first speed. In this case, as indicated by the arrow F in FIG. 10, the tip 12 is further lifted at the second speed. The second speed is equal to or larger than 10 times of the first speed, for example, and is about 70 times of the first speed in the present example. The tip 12 continues to be lifted at the second speed until the tip 12 returns to the standby position.

With the above-mentioned operation, the speed at which the tip 12 is lifted is relatively small until the tip 12 is lifted out from the sample 1. Thus, even in a case where being adsorbed to the sample 1 due to surface tension or the like, the sucked cells 2 are prevented from falling into the sample 1 again. On the other hand, because the speed at which the tip 12 is lifted is relatively large after the tip 12 is lifted out of the sample 1, the tip 12 can return to the standby position in a short period of time. Thus, operability of the cell picking device 100 is improved. Further, the cells 2 can be prevented from being exposed to an atmosphere for a long period of time.

(4) Cell Discharging Operation

FIGS. 11 and 12 are diagrams for explaining a cell discharging operation performed by the suction device 10. As shown in FIG. 11, during the cell discharging operation, the rotator 17 is rotated in a horizontal plane such that the suction arm 11 and the tip 12 are directed toward the plate changer 30. Further, the rotator 35 is rotated in a horizontal plane such that the culture plate 120 is located closer to the suction device 10 than the rack 130. Further, the mover 36 moves in parallel with the horizontal plane such that any well 121 of the culture plate 120 is located below the tip 12 attached to the suction arm 11.

In this state, the suction mechanism of the suction driver 19 operates, so that the cells 2 in the tip 12 are discharged downwardly. Thus, the discharged cells 2 are accommodated in the above-mentioned well 121 of the culture plate 120. After the cells 2 are discharged from the tip 12, the tip detaching mechanism of the suction driver 19 operates, so that the tip 12 is detached from the end of the suction arm 11. The detached tip 12 is discarded to a discarder (not shown).

Thereafter, as shown in FIG. 12, the rotator 35 is rotated in a horizontal plane such that the rack 130 is located closer to the suction device 10 than the culture plate 120. Further, the mover 36 moves in parallel in a horizontal plane such that any replacement tip 131 held by the rack 130 is located below the end of the suction arm 11. In this state, the suction driver 19 moves downwardly. In this case, the above-mentioned replacement tip 131 held by the rack 130 can be attached to the end of the suction arm 11 as a tip 12. Thus, the operation of sucking the cells 2 in FIGS. 3 to 10 can be repeated.

The order of use of wells 121 for accommodating the cells 2 in the culture plate 120 is registered in advance in the controller 50. Similarly, in the rack 130, the order of attachment of replacement tips 131 to the suction arm 11 is registered in advance in the controller 50. In a case where the operation of sucking the cells 2 is repeated, the operation of discharging the cells 2 is repeated with use of a new replacement tip 131 and a well 121 in accordance with the orders in regard to the wells 121 and the replacement tips 131 registered in the controller 50. Thus, the cells 2 can be accommodated in the plurality of wells 121 of the culture plate 120 automatically and in a chronological order.

In the present example, in a case where the number of wells 121 not accommodating the cells 2 in the culture plate 120 (the number of empty wells 121) decreases to a predetermined number, the controller 50 notifies the user. Further, in a case where the number of the replacement tips 131 held by the rack 130 decreases to a predetermined number, the controller 50 notifies the user. The user can prepare a new culture plate 120 or a new rack 130 and place them on the platform 33 at an appropriate point in time by identifying the notifications.

As a way of notification, a character string corresponding to the content of notification may be displayed in the display 40. Alternatively, in a case where the cell picking device 100 includes a sound output device, the sound (including a notification sound such as a buzzer) corresponding to the content of notification may be output from the sound output device. Further, in a case where the cell picking device 100 includes an indicator light such as a lamp, the indicator light may be turned on or off in a manner corresponding to the content of notification.

In a case where the operation of sucking the cells 2 is not repeated in the above-mentioned embodiment, the operation of attaching a new replacement tip 131 to the suction arm 11 in FIG. 12 does not have to be performed. Further, in a case where a tip 12 is not attached to the suction arm 11 in an initial state, an operation of attaching a replacement tip 131 to the suction arm 11 in FIG. 12 is performed before an operation of sucking the cells 2 of FIGS. 3 to 10 is started.

(5) Cell Accommodating Process

Figure 13:
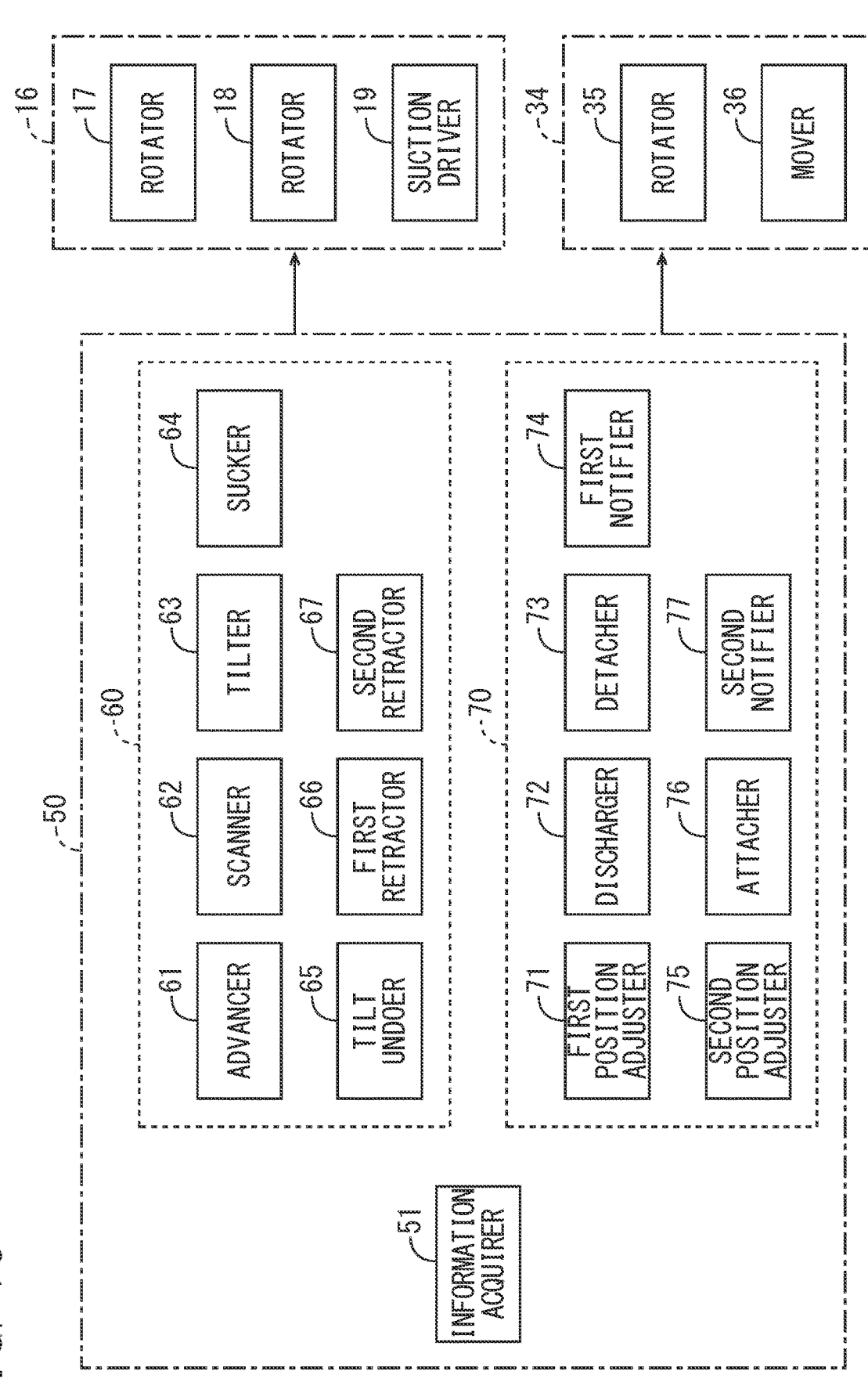
FIG. 13 is a diagram showing the configuration of a controller of FIG. 1.

FIG. 13 is a diagram showing the configuration of the controller 50 of FIG. 1. FIG. 14 is a flowchart showing one example of the algorithm of the cell accommodating process executed by the controller 50. As shown in FIG. 13, the controller 50 includes an information acquirer 51, a suction processor 60 and a discharge processor 70 as functions. Functions of the controller 50 are implemented by execution of a cell accommodating program stored in a memory by the CPU of the controller 50. Part or all of the functions of the controller 50 may be implemented by hardware such as an electronic circuit. The cell accommodating process will be described below with reference to the controller 50 of FIG. 13 and the flowchart of FIG. 14.

First, the information acquirer 51 acquires various information (hereinafter referred to as registration information) registered by the user (step S1). The user can register a position at which cells 2 are likely to be present in the sample container 110 or a position close to the position as a suction position. Further, the user can register the number of times the cells 2 are sucked successively and the number of times the cells 2 are accommodated.

Further, the user can register the information relating to the sample container 110, the culture plate 120 and the rack 130. The information relating to the sample container 110 includes a dimension of the depth of the sample container 110, etc. The information relating to the culture plate 120 includes the number of wells 121 and the order of use of the wells 121 for accommodating the cells 2. The information relating to the rack 130 includes the number of held replacement tips 131 and the order of attachment of the replacement tips 131 to the suction arm 11.

Next, the suction processor 60 executes a cell sucking process (step S2). The cell sucking process is a process of sucking the cells 2 from the sample 1 accommodated in the sample container 110 into the tip 12 based on the registration information acquired in the step S1. Although the tip 12 is attached to the suction arm 11 in an initial state in the present example, in a case where the tip 12 is not attached to the suction arm 11 in the initial state, the steps S26 to S29 of FIG. 16, described below, are performed between the step S1 and the step S2.

Subsequently, the discharge processor 70 executes a cell discharging process (step S3). The cell discharging process is a process of discharging the cells 2 sucked into the tip 12 in the cell sucking process of the step S2 to any well 121 of the culture plate 120 and then replacing the tip 12. Details of the cell sucking process and the cell discharging process will be described below.

Thereafter, an advancer 61, described below, of the suction processor 60 determines whether to continue accommodating the cells 2 (step S4). In a case where the number of times the cells 2 are accommodated is smaller than a registered number (the number acquired in the step S1), the advancer 61 determines to continue accommodating the cells 2 and returns to the step S2. The steps S2 to S4 are repeated until the number of times the cells 2 are accommodated is equal to the registered number. In a case where the number of times the cells 2 are accommodated is equal to the registered number, the advancer 61 determines not to continue accommodating the cells 2 and ends the cell accommodating process.

(6) Cell Sucking Process

FIG. 15 is a flowchart showing one example of the algorithm of the cell sucking process of FIG. 14 executed by the suction processor 60. As shown in FIG. 13, the suction processor 60 includes the advancer 61, a scanner 62, a tilter 63, a sucker 64, a tilt undoer 65, a first retractor 66 and a second retractor 67. The cell sucking process will be described below with reference to the suction arm 11 of FIGS. 3 to 10, the suction processor 60 of FIG. 13 and the flowchart of FIG. 15.

First, the advancer 61 causes the tip 12 attached to the suction arm 11 to advance toward the sample 1 in the sample container 110 by controlling the rotators 17, 18 and the suction driver 19 (FIGS. 3 and 4, and the step S11). Further, the scanner 62 causes the tip 12 to scan the bottom surface of the sample container 110 by controlling the suction driver 19 such that the end of the tip 12 moves toward a suction position acquired in the step S1 (FIG. 5 and the step S12).

Next, the tilter 63 causes the tip 12 to perform a tilt operation by controlling the rotator 18 (FIG. 6 and the step S13). Further, the sucker 64 sucks the cells 2 into the tip 12 by controlling the suction driver 19 (FIG. 7 and the step S14). The step S14 is performed before the end of the step S13. Subsequently, the tilt undoer 65 undoes the tilt operation of the tip 12 by controlling the rotator 18 (FIG. 8 and the step S15).

Thereafter, the scanner 62 determines whether to continue suction (step S16). In a case where successive suction is not carried out, the scanner 62 determines not to continue suction and proceeds to the step S17. In a case where successive suction is carried out, when the number of times the cells 2 are sucked successively is smaller than a registered number (the number acquired in the step S1), the scanner 62 determines to continue suction and returns to the step S12. The steps S12 to S16 are repeated until the number of times the cells 2 are sucked successively is equal to the registered number. In a case where the number of times the cells 2 are sucked successively is equal to the registered number, the scanner 62 determines not to continue suction and proceeds to the step S17.

In the step S17, the first retractor 66 retracts the tip 12 from the sample 1 at a first speed by controlling the suction driver 19 (FIG. 9 and the step S17). Subsequently, the first retractor 66 determines whether the end of the tip 12 has reached a predetermined height (step S18). In a case where the end of the tip 12 has not reached the predetermined height, the steps S17 and S18 are repeated until the end of the tip 12 reaches the predetermined height.

In a case where the end of the tip 12 has reached the predetermined height, the second retractor 67 retracts the tip 12 from the sample 1 at a second speed by controlling the suction driver 19 (FIG. 10 and the step S19). Thereafter, the second retractor 67 determines whether the tip 12 has returned to a standby position (step S20). In a case where the tip 12 has not returned to the standby position, the steps S19 and S20 are repeated until the tip 12 returns to the standby position. In a case where the tip 12 returns to the standby position, the second retractor 67 ends the cell sucking process.

(7) Cell Discharging Process

FIG. 16 is a flowchart showing one example of the algorithm of the cell discharging process of FIG. 14 executed by the discharge processor 70. As shown in FIG. 13, the discharge processor 70 includes a first position adjuster 71, a discharger 72, a detacher 73, a first notifier 74, a second position adjuster 75, an attacher 76 and a second notifier 77 as further functions. The cell discharging process will be described below with reference to the suction arm 11 of FIGS. 11 and 12, the discharge processor 70 of FIG. 13 and the flowchart of FIG. 16.

First, the first position adjuster 71 adjusts the positional relationship between the suction arm 11 and the culture plate 120 by controlling the rotators 17, 18, 35 and the mover 36 in accordance with the order in regard to the wells 121 acquired in the step S1 (FIG. 11 and the step S21). In this case, a well 121 in which cells 2 are to be accommodated next in the culture plate 120 is located below the end of the suction arm 11.

Next, the discharger 72 discharges the cells 2 in the tip 12 by controlling the suction driver 19 (step S22). Thus, the cells 2 are accommodated in the above-mentioned well 121. Subsequently, the detacher 73 detaches the tip 12 from the suction arm 11 by controlling the suction driver 19 (step S23).

Thereafter, the first notifier 74 determines whether the number of empty wells 121 in the culture plate 120 is equal to or larger than a predetermined number based on the number of wells 121 acquired in the step S1 (step S24). In a case where the number of empty wells 121 is equal to or larger than the predetermined number, the first notifier 74 proceeds to the step S26. In a case where the number of empty wells 121 is smaller than the predetermined number, the first notifier 74 notifies the user (step S25) and proceeds to the step S26.

In the step S26, the second position adjuster 75 adjusts the positional relationship between the suction arm 11 and the rack 130 by controlling the rotators 17, 18, 35 and the mover 36 in accordance with the order in regard to the replacement tips 131 acquired in the step S1 (FIG. 12 and the step S26). In this case, a replacement tip 131 to be attached to the suction arm 11 next in the rack 130 is located below the end of the suction arm 11.

Next, the attacher 76 attaches the above-mentioned replacement tip 131 to the suction arm 11 by controlling the suction driver 19 (step S27). Specifically, the replacement tip 131 is attached to the suction arm 11 as a tip 12 by downward movement of the suction arm 11.

Thereafter, the second notifier 77 determines whether the number of replacement tips 131 in the rack 130 is equal to or larger than a predetermined number based on the number of replacement tips 131 acquired in the step S1 (step S28). In a case where the number of replacement tips 131 is equal to or larger than the predetermined number, the second notifier 77 ends the cell discharging process. In a case where the number of replacement tips 131 is smaller than the predetermined number, the second notifier 77 notifies the user (step S29) and ends the cell discharging process.

(8) Effects

In the cell picking device 100 according to the present embodiment, the suction arm 11 advances in the axial direction of the tip 12, such that the end of the tip 12 comes into contact with the bottom surface of the sample container 110 while the tip 12 attached to the suction arm 11 is tilted with respect to the vertical direction. Next, the suction arm 11 is moved such that the end of the tip 12 scans the bottom surface of the sample container 110 in a horizontal direction toward a predetermined position. Subsequently, at the predetermined position, the suction arm 11 is further tilted by a predetermined angle such that the end of the tip 12 is lifted and the base of the tip 12 is lowered. Thereafter, the cells 2 in the sample 1 are sucked through the end of the tip 12 by the sucking operation performed by the suction arm 11.

With this configuration, the end of the tip 12 scans the bottom surface of the sample container 110 toward the predetermined position while being in contact with the bottom surface of the sample container 110, thereby scraping the cells 2 in the sample 1. Here, it is not necessary for the end of the tip 12 to scan the bottom surface of the sample container 110 with high resolution. Therefore, even in a case where the cells 2 and the end of the tip 12 are largely spaced apart from each other, it is possible to efficiently scrap the cells 2 in the sample 1 using the end of the tip 12 by causing the suction arm 11 to scan the bottom surface of the sample container 110. Further, even in a case where the cells 2 are adsorbed to the bottom surface of the sample container 110, because the suction arm 11 is further tilted, the cells 2 that have been scraped by the end of the tip 12 are stripped from the bottom surface of the sample container 110. As a result, the cells 2 in the sample 1 can be sucked efficiently.

(9) Other Embodiments (a) While the suction arm 11 is not configured to be movable in parallel with a horizontal plane in the above-mentioned embodiment, the embodiment is not limited to this. The suction arm 11 may be configured to be movable in parallel with a horizontal plane. Specifically, a mover similar to the mover 36 may be provided in the suction device 10. In this case, the first position adjuster 71 or the second position adjuster 75 may control the mover of the suction device 10 instead of the mover 36. Further, the mover 36 does not have to be provided in the plate changer 30.

(b) While the tilt operation of the tip 12 is undone after the cells 2 are sucked into the tip 12 in the above-mentioned embodiment, the embodiment is not limited to this. In a case where successive suction of the cells 2 is not carried out, etc., the tilt operation of the tip 12 does not have to be undone after the cells 2 are sucked into the tip 12.

(c) While the tip 12 retracts at the first speed until its end reaches the predetermine height and then retracts at the second speed until returning to the standby position in the above-mentioned embodiment, the embodiment is not limited to this. In a case where the sucked cells 2 are not adsorbed to the sample 1, etc., the tip 12 may retract at a constant speed until returning to the standby position.

(d) While the predetermined height during retraction of the tip 12 is the height of a liquid surface of the sample 1 in the above-mentioned embodiment, the embodiment is not limited to this. The predetermined height may be slightly lower than the height of a liquid surface of the sample 1 or slightly higher than the height of a liquid surface of the sample 1.

(e) While the driver 34 includes the rotator 35 in the above-mentioned embodiment, the embodiment is not limited to this. In a case where the culture plate 120 and the rack 130 can be selectively moved to the vicinity of the suction device 10 by sufficiently large movement of the platform 33 by the mover 36 in a horizontal plane, the driver 34 does not have to include the rotator 35.

(f) While the tip 12 of the suction arm 11 is replaced automatically in the above-mentioned embodiment, the embodiment is not limited to this. The tip 12 of the suction arm 11 may be replaced manually by a user. In this case, the driver 34 does not have to include the rotator 35, and the controller 50 does not have to include the detacher 73, the second position adjuster 75, the attacher 76 or the second notifier 77.

(g) While the cell picking device 100 includes the plate changer 30 in the above-mentioned embodiment, the embodiment is not limited to this. The plate changer 30 is an optional device, and the cell picking device 100 does not have to include the plate changer 30. Therefore, the cells 2 sucked by the tip 12 do not have to be discharged to the culture plate 120 and may be discarded, for example.

(10) Aspects

It is understood by those skilled in the art that the plurality of above-mentioned illustrative embodiments are specific examples of the below-mentioned aspects.

(Item 1) A cell picking device according to one aspect for sucking cells from a liquid sample in a sample container, may include a suction arm to which a pipette tip is attachable, a first driver that drives the suction arm and causes the suction arm to perform a sucking operation, and a controller that controls an operation of the first driver, wherein the controller may include an advancer that advances the suction arm in an axial direction of the pipette tip such that an end of the pipette tip comes into contact with a bottom surface of the sample container while tilting the pipette tip attached to the suction arm with respect to a vertical direction, a scanner that moves the suction arm such that an end of the pipette tip scans a bottom surface of the sample container in a horizontal direction toward a predetermined position, a tilter that further tilts the suction arm by a predetermined angle such that an end of the pipette tip is lifted and a base of the pipette tip is lowered at the predetermined position, and a sucker that causes the suction arm to perform a sucking operation such that a sample is sucked through an end of the pipette tip.

In this cell picking device, the suction arm advances in the axial direction of the pipette tip such that the end of the pipette tip comes into contact with the bottom surface of the sample container while the pipette tip attached to the suction arm is tilted with respect to a vertical direction. Next, the suction arm is moved such that the tip of the pipette tip scans the bottom surface of the sample container in a horizontal direction toward a predetermined position. Subsequently, at the predetermined position, the suction arm is further tilted by a predetermined angle such that the end of the pipette tip is lifted and the base of the pipette tip is lowered. Thereafter, the suction operation is performed by the suction arm, so that the cells in the sample are sucked through the end of the pipette tip.

With this configuration, the end of the pipette tip scans the bottom surface of the sample container toward the predetermined position while being in contact with the bottom surface of the sample container. Thus, the cells in the sample are scraped by the end of the pipette tip. Here, it is not necessary for the end of the pipette tip to scan the bottom surface of the sample container with high resolution. Therefore, even in a case where the cells and the end of the pipette tip are largely spaced apart from each other, it is possible to efficiently scrape the cells in the sample using the end of the pipette tip by scanning the bottom surface of the sample container using the suction arm. Further, even in a case where the cells are adsorbed to the bottom surface of the sample container, because the suction arm is further tilted, the cells that have been scraped by the end of the pipette tip are stripped from the bottom surface of the sample container. As a result, the cells in the sample can be sucked efficiently.

(Item 2) The cell picking device according to item 1, wherein the sucker may cause the suction arm to start performing a sucking operation in a period before tilt control with respect to the suction arm is stopped, after the tilt control with respect to the suction arm by the tilter is started.

In this case, cells that have been scraped from the bottom surface of the sample container by the end of the pipette tip can be sucked efficiently.

(Item 3) The cell picking device according to item 1 or 2, wherein the controller may further include a tilt undoer that undoes a tilt of the suction arm by the tilter after control for a sucking operation performed by the sucker is stopped.

In this case, an attitude of the pipette tip after cells are sucked returns to an attitude before the suction arm is tilted. Therefore, cells can be sucked successively as described above by simple control.

(Item 4) The cell picking device according to item 1 or 2, wherein the predetermined angle may be larger than 0 degree.

In this case, cells can be easily stripped from the bottom surface of the sample container.

(Item 5) The cell picking device according to item 1 or 2, wherein the predetermined angle may be equal to or smaller than 2 degrees.

In this case, the position of the end of the pipette tip hardly changes. Therefore, the user can easily magnify and observe the end of the pipette tip.

(Item 6) The cell picking device according to item 1 or 2, wherein the controller may include a first retractor that retracts the suction arm at a first speed in the axial direction until an end of the pipette tip reaches a predetermined height after control for a sucking operation performed by the sucker is stopped, and a second retractor that retracts the suction arm at a second speed larger than the first speed in the axial direction after an end of the pipette tip reaches the predetermined height.

In this case, the retracting speed of the pipette tip is relatively small until the end of the pipette tip reaches the predetermined height. Thus, even in a case where being adsorbed to a sample due to surface tension or the like, sucked cells are prevented from falling into a sample again. On the other hand, after the end of the pipette tip reaches the predetermined height, the retracting speed of the pipette tip is relatively large. Therefore, retraction of the pipette tip is completed in a short period of time. Thus, operability of the cell picking device can be improved.

(Item 7) The cell picking device according to item 6, wherein the second speed may be equal to or larger than 10 times of the first speed.

In this case, because the retracting speed of the pipette tip is relatively small until the end of the pipette tip reaches the predetermine height, cells are sufficiently prevented from falling into a sample again. On the other hand, after the end of the pipette tip reaches the predetermined height, the retracting speed of the pipette tip is relatively large. Thus, retraction of the pipette tip can be completed in a shorter period of time.

(Item 8) The cell picking device according to item 6, wherein the predetermined height may be a height of a liquid surface of a sample in the sample container.

In this case, because the retracting speed of the pipette tip is relatively small until the end of the pipette tip is separated from a sample, cells are more reliably prevented from falling into a sample again. On the other hand, after the end of the pipette tip is separated from a sample, the retraction of the pipette tip can be completed in a short period of time. Further, cells can be prevented from being exposed to an atmosphere for a long period of time.

(Item 9) The cell picking device according to item 1 or 2, may further include a platform on which a culture plate in which a plurality of wells are arranged is placeable, and a second driver that drives the platform, wherein the controller may further include a first position adjuster that controls the first or second driver such that a position of a well accessible by the suction arm changes sequentially in the culture plate, and a discharger that causes the suction arm to perform a discharging operation such that a sample is discharged through an end of the pipette tip, and a sucking operation performed by the sucker and a discharging operation performed by the discharger may be controlled alternately.

In this case, sucked cells can be accommodated successively in a plurality of wells of the culture plate.

(Item 10) The cell picking device according to item 9, wherein a pipette tip rack that holds a plurality of replacement pipette tips may be further placed on the platform, the first driver may be configured to be capable of detaching the pipette tip from the suction arm, and the controller may further include a detacher that controls the first driver so as to detach the pipette tip from the suction arm, a second position adjuster that controls the first or second driver such that a position of a replacement pipette tip accessible by the suction arm changes sequentially in the pipette tip rack, and an attacher that controls the first or second driver such that any replacement pipette tip in the pipette tip rack is attached to the suction arm as the pipette tip, and a sucking operation performed by the sucker, a discharging operation performed by the discharger, detachment of the pipette tip by the detacher and attachment of the pipette tip by the attacher may be controlled alternately.

In this case, after cells are discharged to any well of the culture plate from the pipette tip, the pipette tip is detached from the suction arm. Further, any replacement pipette tip in the pipette tip rack is attached to the suction arm, and cells are sucked by the pipette tip. Thus, the sucked cells can be accommodated in a plurality of wells of the culture plate automatically and successively.

(Item 11) The cell picking device according to item 10, wherein the second driver may include a rotator that rotates the platform in a horizontal plane, the first position adjuster may rotate the rotator such that the culture plate is located closer to the suction arm than the pipette tip rack when a discharging operation performed by the discharger is controlled, and the second position adjuster may rotate the rotator such that the pipette tip rack is located closer to the suction arm than the culture plate when attachment of the pipette tip by the attacher is controlled.

In this case, it is possible to selectively move the culture plate and the pipette tip rack to a position accessible by the suction arm without increasing a moving range of the platform.

The invention claimed is:

1. A cell picking device for sucking cells from a liquid sample in a sample container using a pipette tip, comprising:
a suction arm configured to receive the pipette tip, such that the pipette tip is attached to the suction arm;
a first driver configured to drive the suction arm and cause the suction arm to perform a sucking operation; and
a controller that controls an operation of the first driver, wherein the controller is configured to:
cause the first driver to advance the suction arm in an axial direction of the pipette tip and to tilt the pipette tip such that an end of the pipette tip comes into contact with a bottom surface of the sample container and to tilt the suction arm relative to a vertical direction such that the pipette tip attached to the suction arm is bent at a first tilt angle by the bottom surface of the sample container,
cause the first driver to move the suction arm such that the end of the pipette tip scans the bottom surface of the sample container in a horizontal direction toward a predetermined position,
cause the first driver to further tilt the suction arm by a predetermined angle by rotating the pipette tip such that the pipette tip is bent at a second tilt angle that is more horizontal than the first tilt angle, and
cause the suction arm to perform a sucking operation such that a sample is sucked through the end of the pipette tip by:
causing the suction arm to advance towards and press the end of the pipette tip against the bottom surface of the sample container, such that an elastic material of the pipette tip is bent due to the pressing of the end of the pipette tip against the bottom surface of the sample container, and
while the end of the pipette tip is bent and is in contact with the bottom surface of the sample container, cause the suction arm to move such that the pipette tip:
scans the bottom surface of the sample container in a horizontal direction; and
separates cells adsorbed to the bottom surface of the sample container.

2. The cell picking device according to claim 1, wherein the controller causes the suction arm to start performing a sucking operation in a period between starting and stopping tilt control with respect to the suction arm.

3. The cell picking device according to claim 1, wherein the controller is further configured to control the suction arm to undo a tilt of the suction arm after control for a sucking operation is stopped.

4. The cell picking device according to claim 1, wherein the predetermined angle is larger than 0 degree.

5. The cell picking device according to claim 1, wherein the predetermined angle is equal to or smaller than 2 degrees.

6. The cell picking device according to claim 1, wherein the controller is further configured to:
cause the first driver to retract the suction arm at a first speed in the axial direction until an end of the pipette tip reaches a predetermined height after control for a sucking operation is stopped, and cause the first driver to retract the suction arm at a second
speed larger than the first speed in the axial direction
after an end of the pipette tip reaches the predetermined
height.

7. The cell picking device according to claim 6, wherein
the second speed is equal to or larger than 10 times of the
first speed.

8. The cell picking device according to claim 6, wherein
the predetermined height is a height of a liquid surface of
a sample in the sample container.

9. The cell picking device according to claim 1, further
comprising:

a platform configured to receive a culture plate including
a plurality of wells, and a second driver that drives the platform, wherein the controller is further configured to:

control the first or second driver such that a position of
a well included in the plurality of wells accessible by
the suction arm changes sequentially in the culture
plate, and cause the suction arm to perform a discharging opera-
tion such that a sample is discharged through an end
of the pipette tip, and cause the suction arm to alternatively perform the
sucking operation and the discharging operation.

10. The cell picking device according to claim 9, further
comprising:

a pipette tip rack placed on the platform and configured to
hold a plurality of replacement pipette tips, wherein the first driver is configured to detach the pipette
tip from the suction arm, and the controller is further
configured to:

control the first driver to detach the pipette tip from the
suction arm, control the first or second driver such that a position of
a replacement pipette tip included in the plurality of
replacement pipette tips accessible by the suction
arm changes sequentially in the pipette tip rack, control the first or second driver such that any replace-
ment pipette tip included in the plurality of replace-
ment pipette tips in the pipette tip rack is attached to
the suction arm as the pipette tip, and control alternatively alternately a sucking operation, a
discharging operation, detachment of the pipette tip,
and attachment of the pipette tip.

11. The cell picking device according to claim 10, wherein
the second driver includes a rotator that rotates the
platform in a horizontal plane, the controller is configured to cause the rotator to rotate
such that the culture plate is located closer to the
suction arm than the pipette tip rack when the discharg-
ing operation is performed, and the controller is configured to cause the rotator to rotate
such that the pipette tip rack is located closer to the
suction arm than the culture plate when attaching the
pipette tip.

* * * * *